(12) United States Patent
Tsuji et al.

(10) Patent No.: US 6,350,865 B1
(45) Date of Patent: Feb. 26, 2002

(54) PROCESS FOR THE PREPARATION OF PENTAACETYL-β-D-GLUCOPYRANOSE

(75) Inventors: Masahiro Tsuji; Hiroyuki Yamazaki, both of Saitama-ken (JP)

(73) Assignee: Nisshin Pharma Inc., Tokyo (JP)

( * ) Notice: Subject to any disclaimer, the term of this patent is extended or adjusted under 35 U.S.C. 154(b) by 0 days.

(21) Appl. No.: 09/506,386

(22) Filed: Feb. 18, 2000

(30) Foreign Application Priority Data

Feb. 19, 1999 (JP) ............................................ 11-041937

(51) Int. Cl.$^7$ ............................................... C07H 15/00
(52) U.S. Cl. ...................... 536/18.6; 536/18.5; 536/4.1; 536/112
(58) Field of Search ............................... 536/18.6, 18.5, 536/4.1, 112

(56) References Cited

FOREIGN PATENT DOCUMENTS

JP      2000178294    *  6/2000

OTHER PUBLICATIONS

Hua et al. "A convenient method for the preparation of alpha– and beta– D– 1,2,3,4,6–penta–O–acetylglucopyranose." CAPLUS. 117:26931. Huaxue Tongbao, (1992), (2), 33–34.*

Hashimoto et al. "A convenient one–pot preparation of glycosyl bromides as well as glycosyl acetates from benzyl glycosides using N–bromosuccinimide." CAPLUS. 108:187086. Tetrahedron Lett. (1987), 28(30), 3505–8.*

Limousine, et al. "Solvent–free synthesis of decayl d–glucopyranosides under focused microwave irradiation" Journal of Carbohydrate Chemistry, US, New York, NY—vol. 16, No. 3, 1997 pp. 327–342.

Shimiu H, et al. "Chemical Synthesis of C–Labelled Ganglioside Gb3 Thrisaccharide from 'U–C!–D–Glucose" Tetrahedron, NL, Elsevier Science Publishers, Amsterdam—vol. 54, No. 32 Aug. 6, 1998 pp. 9489–9506 XPoo4127421.

"Methods in Carbohydrate Chemistry", M. L. Wolfrom et al., vol. 2, Academic Press, (1963), pp. 211–215.

* cited by examiner

Primary Examiner—Ralph Gitmore
Assistant Examiner—Devesh Khare
(74) Attorney, Agent, or Firm—McDermott, Will & Emery

(57) ABSTRACT

In a process for the preparation of pentaacetyl-β-D-glucopyranose by reacting D-glucose with acetic anhydride in the presence of sodium acetate catalyst, the improvement is provided wherein 5–10 mols of acetic anhydride are used per mol of D-glucose and the reaction is performed in an organic solvent. Pentaacetyl-β-D-glucopyranose is useful as intermediates for the synthesis of raw materials for industrial chemicals, medicines, cosmetics and the like.

4 Claims, No Drawings

PROCESS FOR THE PREPARATION OF PENTAACETYL-β-D-GLUCOPYRANOSE

FIELD OF THE INVENTION

This invention relates to an improved process for the preparation of pentaacetyl-β-D-glucopyranose useful as intermediates for the synthesis of raw materials for industrial chemicals, medicines and cosmetics, for example, Arbutin or its related compounds, and the like. More particularly, the invention relates to a process of preparing pentaacetyl-β-D-glucopyranose of high purity in high yield.

BACKGROUND OF THE INVENTION

A process for the preparation of pentaacetyl-β-D-glucopyranose is described by M. L. Wolfrom and A. Thompson in "Methods in Carbohydrate Chemistry, vol. 2, Academic Press, pp. 211–212 (1963)". This method performs an acetylation of D-glucose with acetic anhydride at high temperature in the presence of sodium acetate catalyst.

In the method described in the above-mentioned literature, acetic anhydride is used in an amount of 13 mols per mol of D-glucose, that is, in an excess amount corresponding to 2.6 times a theoretical amount. However, a problem arises that the reaction of such an excess amount of acetic anhydride with D-glucose at a high temperature (e.g., 100° C.) in the presence of sodium acetate catalyst will bring about a rapid progress of reaction, leading to the difficulty in control. In this method, it is assumed that an addition of acetic anhydride in more than two times amount to five reaction sites (hydroxyl groups) in D-glucose will result in rapid progress of reaction.

For the preparation of pentaacetyl-β-D-glucopyranose, the above reference method has performed the acetylation of D-glucose as follows:

"50 g of anhydrous sodium acetate and 700 ml of acetic anhydride are placed in a 2-liter, round-bottomed flask, and heated over a flame to the boiling point in a hood. About 3 g of anhydrous D-glucose from a 100 g supply is added, the flask, without shaking, is heated carefully at the point nearest the sugar laying on the bottom. Initiation of the reaction is indicated by continued boiling after removal of the flame. Then, the flame is extinguished and the flask is placed on a cork ring. The remainder of the sugar is added in small portions at a rate which maintains the boiling temperature of the mixture. The flask is occasionally shaken to prevent an accumulation of solid sugar on the bottom of the flask. If the reaction stops, it should be started again by heating before much more sugar is added to the flask. After the addition of all the sugar and after the reaction has subsided, the solution is brought to a full boil." (See p. 212 of the same literature.)

Thus, the above reference method has taken a measure of conducting careful reaction, while adding D-glucose in small portions, to prevent a rapid progress of reaction.

Such a series of complicated steps makes an industrial production very difficult. Further, the above-mentioned literature describes in the middle of page 212 as follows: "The reaction solution is cooled and poured with stirring onto 2 liters of cracked ice. After standing 3 hours with occasional stirring, the crystalline material is filtered and washed with cold water. Yield 160 g (73%)." The yield is not satisfactory. About the purification of the crude product, there is the following description:

"Purification is effected by recrystallization from 1 liter of hot 95% ethanol followed by filtration with decolorizing carbon. The product is filtered as soon as the temperature of the crystalline material has cooled to room temperature. Further recrystallization in the same manner produces pure pentaacetyl-β-D-glucopyranose." However, this method requires a treatment with decolorizing carbon or the like, and takes a lot of time and labor in the purification. In addition, the method requires twice recrystallization for the preparation of pure pentaacetyl-β-D-glucopyranose. Though there is no reference to a yield of the purified product, it is presumed to be about 50–60%. Therefore, there is a demand for a process for the preparation of pentaacetyl-β-D-glucopyranose in a satisfactory yield under industrially practicable reaction conditions.

DISCLOSURE OF THE INVENTION

As a result of extensive investigation in an effort to prepare pentaacetyl-β-D-glucopyranose efficiently, the present inventors have found that pentaacetyl-β-D-glucopyranose of high-purity can be prepared in high yield under very mild reaction conditions by using acetic anhydride of 1–2 times the theoretical amount relative to D-glucose and performing the reaction in an organic solvent in the preparation of pentaacetyl-β-D-glucopyranose by reacting acetic anhydride with D-glucose in the presence of sodium acetate catalyst.

Thus the present invention provides a process for the preparation of pentaacetyl-β-D-glucopyranose by reacting D-glucose with acetic anhydride in the presence of sodium acetate catalyst, characterized in that 5–10 mols of acetic anhydride are used per mol of D-glucose and the reaction is performed in an organic solvent.

An amount of acetic anhydride used in the invention is theoretically enough in one mol per mol of a hydroxyl group in D-glucose, but up to 2 mols will not be an obstacle to the control of reaction. However, more than 2 mols are not preferable, since the reaction proceeds with violence. Less than one mol ratio is not preferable, since an acetylation of D-glucose does not proceed completely, leaving hydroxyl group(s) unreacted, which results in lowering a yield of a desired end product.

The solvents used in the invention can include aliphatic hydrocarbons such as pentane, hexane, heptane, petroleum ether and the like; aromatic hydrocarbons such as benzene, toluene, xylene and the like; acetic acid esters such as ethyl acetate, propyl acetate, isopropyl acetate, isobutyl acetate, butyl acetate and the like; chlorinated hydrocarbons such as chloroform, carbon tetrachloride, 1,2-dichloroethane and the like. They are preferably used alone, but may be used in combination with some kinds of organic solvents. The organic solvents are used in the amount of 5–20 times by volume, preferably 5–10 times by volume, per part by weight of D-glucose. For example, the amount of 5 times by volume of the organic solvent per part by weight of D-glucose means 150 ml of the organic solvent relative to 30 g of D-glucose.

The sodium acetate catalyst can be used in the amount of 0.1–1 mol, preferably 0.1–0.5 mol, per mol of D-glucose.

Usually, the reaction is carried out by heating a mixture of D-glucose, acetic anhydride and sodium acetate in the organic solvent. This reaction is preferably carried out at boiling point of the reaction solvent used, i.e., under reflux. The reaction time ranges from 30 minutes to 24 hours, depending on kinds of the reaction solvents used and other factors.

After completion of the reaction, water is added to the reaction mixture to decompose unreacted acetic anhydride. The reaction mixture is neutralized with an aqueous alkali solution, and the organic layer is separated. The organic layer is washed with water, if necessary.

The solvent is evaporated off from the organic layer and the resultant crude crystals of pentaacetyl-β-D-glucopyranose are crystallized in a solvent for recrystallization such as ethanol, or alternatively a part of the organic solvent is distilled off from the organic layer and the desired pentaacetyl-β-D-glucopyranose is crystallized from the remaining solution, by which a purified product can be obtained.

Thus, according to the invention, pentaacetyl-β-D-glucopyranose of high-purity can be prepared in high yield by an industrially practicable method.

The invention is illustrated, but in no way limited, by the following examples.

EXAMPLE 1

A mixture of D-glucose (30.0 g, 0.167 mol), acetic anhydride (142 ml, 1.51 mol), sodium acetate (3.0 g, 0.0366 mol) and butyl acetate (150 ml) was refluxed with stirring for one hour and 30 minutes. To this reaction mixture was added water (100 ml), the mixture was stirred and neutralized with a 3% sodium hydroxide solution. The organic layer was concentrated to give 62.0 g (yield 95%) of pentaacetyl-β-D-glucopyranose as crude crystals. The crude crystals contained 13% of pentaacetyl-α-D-glucopyranose, but recrystallization from ethanol gave 48.7 g (yield 75%) of pure pentaacetyl-β-D-glucopyranose. Melting point 132° C.

EXAMPLE 2

A mixture of D-glucose (30.0 g, 0.167 mol), acetic anhydride (100 ml, 1.06 mol), sodium acetate (5.0 g, 0.0609 mol) and toluene (250 ml) was refluxed with stirring for 3 hours. To this reaction mixture was added water (100 ml), the mixture was stirred and neutralized with a 3% sodium hydroxide solution. After the organic layer was concentrated to halves, precipitated crystals were filtered off to give 50.0 g (yield 77%) of pure pentaacetyl-β-D-glucopyranose.

EXAMPLE 3

A mixture of D-glucose (30.0 g, 0.167 mol), acetic anhydride (142 ml, 1.51 mol), sodium acetate (3.0 g, 0.0366 mol) and benzene (250 ml) was refluxed with stirring for one hour and 30 minutes. To this reaction mixture was added water (100 ml), the mixture was stirred and neutralized with a 3% sodium hydroxide solution. After the organic layer was concentrated to give crude crystals, recrystallization from ethanol gave 48.1 g (yield 73%) of pure pentaacetyl-β-D-glucopyranose.

EXAMPLE 4

A mixture of D-glucose (3.0 g, 16.7 mmol), acetic anhydride (10 ml, 151 mmol), sodium acetate (0.3 g, 3.66 mmol) and hexane (25 ml) was refluxed with stirring for 13 hours. To this reaction mixture was added toluene (25 ml) and water (20 ml), the mixture was stirred and neutralized with a 3% sodium hydroxide solution. After the organic layer was concentrated to give crude crystals, recrystallization from ethanol gave 4.6 g (yield 70%) of pure pentaacetyl-β-D-glucopyranose.

EXAMPLE 5

A mixture of D-glucose (3.0 g, 16.7 mmol), acetic anhydride (10 ml, 151 mmol), sodium acetate (0.3 g, 3.66 mmol) and chloroform (25 ml) was refluxed with stirring for 24 hours. To this reaction mixture was added water (10 ml), the mixture was stirred and neutralized with a 3% sodium hydroxide solution. After the organic layer was concentrated to give crude crystals, recrystallization from ethanol gave 4.4 g (yield 68%) of pure pentaacetyl-β-D-glucopyranose.

According to the invention, pentaacetyl-β-D-glucopyranose useful as intermediates for the synthesis of raw materials for industrial chemicals, medicines and cosmetics, for example, Arbutin or its related compounds, and the like can be prepared in high purity and high yield in the industrial scale.

What is claimed is:

1. A process for the preparation of pentaacetyl-β-D-glucopyranose by reacting D-glucose with acetic anhydride in the presence of sodium acetate catalyst, the improvement wherein 5–10 mols of acetic anhydride are used per mol of D-glucose and the reaction is performed in an organic solvent under reflux.

2. The process of claim 1 wherein the sodium acetate catalyst is used in the amount of 0.1–1 mol per mol of D-glucose.

3. The process of claim 1 wherein the organic solvent is selected from the group consisting of an aliphatic hydrocarbon, an aromatic hydrocarbon, an acetic acid ester, a chlorinated hydrocarbon and the combination thereof.

4. The process of claim 1 wherein the organic solvent is used in the amount of 5–20 times by volume per part by weight of D-glucose.

* * * * *